(12) United States Patent
Dellaca et al.

(10) Patent No.: US 11,524,131 B2
(45) Date of Patent: Dec. 13, 2022

(54) DEVICE FOR FACILITATING THE ADMINISTRATION OF A MEDICAMENT TO THE LUNG BY A CATHETER

(71) Applicant: CHIESI FARMACEUTICI S.p.A., Parma (IT)

(72) Inventors: Raffaele Dellaca, Parma (IT); Ilaria Milesi, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 221 days.

(21) Appl. No.: 16/344,180

(22) PCT Filed: Oct. 11, 2017

(86) PCT No.: PCT/EP2017/075991
§ 371 (c)(1),
(2) Date: Apr. 23, 2019

(87) PCT Pub. No.: WO2018/077623
PCT Pub. Date: May 3, 2018

(65) Prior Publication Data
US 2019/0314592 A1    Oct. 17, 2019

(30) Foreign Application Priority Data

Oct. 26, 2016   (EP) .................................. 16195826

(51) Int. Cl.
*A61M 16/04*   (2006.01)
*A61B 17/24*   (2006.01)
(Continued)

(52) U.S. Cl.
CPC ......... *A61M 16/0488* (2013.01); *A61B 17/24* (2013.01); *A61M 11/02* (2013.01);
(Continued)

(58) Field of Classification Search
CPC ...... A61B 17/24; A61K 9/0082; A61M 11/02; A61M 16/00; A61M 16/0418;
(Continued)

(56) References Cited

U.S. PATENT DOCUMENTS 5,788,680 A * 8/1998 Linder .............. A61M 25/0068
604/264
5,803,078 A * 9/1998 Brauner ............ A61M 16/0484
128/207.14
(Continued)

FOREIGN PATENT DOCUMENTS

DE   10 2010 025 045 A1   12/2011
GB            2444779 A *  6/2008   ........ A61M 16/0484
(Continued)

OTHER PUBLICATIONS

International Search Report and Written Opinion dated Nov. 17, 2017 in PCT/EP2017/075991 filed on Oct. 11, 2017.
(Continued)

*Primary Examiner* — Justine R Yu
*Assistant Examiner* — Matthew D Ziegler
(74) *Attorney, Agent, or Firm* — Oblon, McClelland, Maier & Neustadt, L.L.P.

(57) ABSTRACT

A device (100) for facilitating the positioning of a catheter for the administration of a liquid medicament to a spontaneously breathing patient. The method and system according to preferred embodiments of the present invention allows optimizing the dispensing said medicaments. In particular the system according to a preferred embodiment of the present invention allows the administration of an exogenous pulmonary surfactant to preterm patients.

13 Claims, 5 Drawing Sheets

(51) Int. Cl.
*A61M 11/02* (2006.01)
*A61M 16/08* (2006.01)

(52) U.S. Cl.
CPC ..... *A61M 16/0463* (2013.01); *A61M 16/0486* (2014.02); *A61M 16/0858* (2014.02); *A61M 2202/0488* (2013.01); *A61M 2210/1046* (2013.01); *A61M 2240/00* (2013.01)

(58) Field of Classification Search
CPC .......... A61M 16/0431; A61M 16/0463; A61M 16/0486; A61M 16/0488; A61M 16/0497; A61M 16/0858; A61M 31/00; A61M 2039/0252; A61M 2202/0488; A61M 2209/06; A61M 2210/1046; A61M 2240/00; A61M 25/0067; A61M 25/0068; A61M 25/007
USPC .................................................. 128/207.14
See application file for complete search history.

(56) References Cited

U.S. PATENT DOCUMENTS

| | | | | |
|---|---|---|---|---|
| 6,196,224 | B1 | 3/2001 | Alfery | |
| 6,526,976 | B1* | 3/2003 | Baran | A61M 25/003 |
| | | | | 128/207.14 |
| 6,631,720 | B1* | 10/2003 | Brain | A61M 16/0486 |
| | | | | 128/207.14 |
| 7,992,562 | B2* | 8/2011 | Chen | A61M 16/0409 |
| | | | | 128/207.14 |
| 8,393,328 | B2* | 3/2013 | Angel | A61M 16/0479 |
| | | | | 128/207.14 |
| 8,631,796 | B2* | 1/2014 | Cook | A61M 16/0431 |
| | | | | 128/207.15 |
| 8,690,756 | B2* | 4/2014 | Deal | A61B 1/00101 |
| | | | | 600/106 |
| 8,864,791 | B2* | 10/2014 | Bloom | A61M 16/0418 |
| | | | | 606/200 |
| 9,993,607 | B2* | 6/2018 | Weaver | A61M 16/1005 |
| 10,058,668 | B2* | 8/2018 | Wondka | A61B 5/082 |
| 2007/0197998 | A1* | 8/2007 | Itou | A61M 25/002 |
| | | | | 604/523 |
| 2008/0230054 | A1 | 9/2008 | Prineas | |
| 2013/0277443 | A1 | 10/2013 | Croll et al. | |
| 2013/0333695 | A1 | 12/2013 | Dellaca et al. | |
| 2014/0014113 | A1* | 1/2014 | Ali | A61M 16/0431 |
| | | | | 128/207.15 |
| 2016/0101255 | A1* | 4/2016 | Kumpel | A61M 16/0497 |
| | | | | 128/207.15 |
| 2017/0065782 | A1* | 3/2017 | Acha Gandarias | |
| | | | | A61M 16/0415 |

FOREIGN PATENT DOCUMENTS

| | | |
|---|---|---|
| GB | 2 456 815 A | 7/2009 |
| KR | 20-2016-0002937 U | 8/2016 |
| WO | WO 00/18461 A1 | 4/2000 |
| WO | WO 2005/089634 A1 | 9/2005 |
| WO | WO 2012/054013 A1 | 4/2012 |
| WO | WO 2013/160129 A1 | 10/2013 |

OTHER PUBLICATIONS

European Search Report dated Mar. 17, 2017 in European Application No. 16195826.9 filed on Oct. 26, 2016.

* cited by examiner

DEVICE FOR FACILITATING THE ADMINISTRATION OF A MEDICAMENT TO THE LUNG BY A CATHETER

CROSS REFERENCE TO RELATED APPLICATIONS

This application is a 371 application of International Patent Application No. PCT/EP2017/075991, filed on Oct. 11, 2017, and claims priority to European Patent Application No. 16195826.9, filed on Oct. 26, 2016, both of which are incorporated herein by reference in their entireties.

FIELD OF TECHNOLOGY

The present invention relates to the field of instillation of medicament and particularly to a device for facilitating the administration of a liquid or aerosol medicament to the lung (e.g. a pulmonary surfactant), by a thin catheter.

BACKGROUND OF THE INVENTION

Administration of medicament in the lungs often faces with the problem of finding a right balance between the treatment efficacy and the invasiveness of the method. This is particularly true for infants (hereinafter the term neonates is used as synonymous of infants). Among other diseases, pre-term neonates may be affected by nRDS (neonatal Respiratory Distress Syndrome), a respiratory disease due to generalized lung immaturity which causes pulmonary surfactant deficiency. For many years, nRDS has been treated by administration of exogenous pulmonary surfactants as bolus through endotracheal instillation to the intubated preterm neonates kept under mechanical ventilation at least for a very brief time. Although this treatment is very effective, as proven by the reduced mortality and improved long term quality of life, it may present some drawbacks. On one side there are the intrinsic drawbacks of the mechanical ventilation (volu/barotrauma) and to the intubation procedure which is anyway invasive and may lead to chronic lung disease (also known as bronchopulmonary dysplasia).

One the other hand the administration of a bolus may have systemic effect, such as fast variation in cerebral blood flow, due to the administration of a big amount of liquid, compared to tidal volume, into the lungs.

In view of the potential complications in intubated neonates at birth, scientific attention has been focused on different approaches of exogenous pulmonary surfactants administration of exogenous pulmonary surfactants aiming at avoiding or limiting the use of invasive mechanical ventilation.

Moreover, the new guidelines for the treatment of the preterm infants suggest avoiding the use of invasive ventilation whenever it is possible and preferring non-invasive approaches, which means that infants are no longer intubated if it is not strictly necessary and consequently they would be intubated just for the administration of the surfactant. All these modalities rely on the premise that preterm infants are mainly nose-breathers, thus all the interfaces developed for the ventilatory support, provide gas flow at the nose by means of nasal prongs, nasal cannulae, nasal masks and so on.

In particular, as a possible respiratory support, the use of non-invasive ventilation modalities such as early nasal Continuous Positive Airway Pressure (nCPAP) or High Flow Nasal Cannula (HFNC), that delivers air into the lungs through specifically designed nasal devices such as masks, prongs or tubes, has been introduced in neonatal intensive care units (NICUs).

Nasal CPAP therapy aims to support neonates, especially pre-term and low-birth weight newborns, who can breathe spontaneously but inadequately. The therapy is non-invasive, low cost, clinically effective and safe. When applied properly and promptly, nasal CPAP could minimize both the need for intubation and mechanical ventilation and promote early extubation, as well as decrease incidence of chronic lung disease. HFNC is a recent modality of ventilation that is put aside to nCPAP. HFNC consists in providing high flow of heated and humidified air by means of nasal prongs although it is still under the evaluation of the Scientific Community, it is well accepted in NICUs thanks to the facility in the management and to very promising results.

Following this orientation, in the last fifteen years great attention has also been paid to find out alternative less invasive way for pulmonary surfactant administration, possibly in combination with non-invasive ventilation supports.

For example, the use of a gastric tube placed in the trachea supported with nCPAP has been proposed in WO 2008/148469. Similar devices such as vascular catheters or nasogastric tubes were also disclosed in the art (Dargaville P A et al Arch Dis Fetal Neonatal Ed 2013, 98(2), 122-126; Aguar M et al Acta Paediatrica, ISSN 0803-5253, first published on-line on Mar. 15, 2014).

As an alternative approach, surfactant atomization was proposed in Wagner M et al Crit Care Med 2000, 28, (7), 2540-2544.

In this respect, WO2013/160129 discloses a method and system for delivering by atomization an aerosol medicament to a patient, including: a thin multi lumen flexible catheter to be inserted in the retro-pharyngeal region of the patient.

The above mentioned document discloses a method and system which makes use of air/blasting technique to deliver atomized particles to the lungs, optimizing the dispensing of surfactant without invasive operations. The described solution provides several advantages including: a more gentle atomizing process, thanks to the air-blasting atomizing catheter, whose mechanical impact on the surfactant is minimal; an easier manufacturing and a more compact design of the atomizing catheter. One of the key advantages of such method and system is that it could be used during non-invasive mechanical ventilation, CPAP and spontaneous breathing.

However, in order to properly exploit the advantages of the aforementioned methods and systems, a device for facilitating the insertion and correctly positioning the catheter is required.

Preferably, said device should be able to get to its appropriate position without the need of visual inspection devices such as fiberscopes and/or other common state of the art tools such Magill forceps.

On the other hand, said device should not impede either the breathing airflow and, should be compatible with respiratory support systems such as nasal Continuous Positive Airway Pressure (CPAP) or High Flow Nasal Cannula (HFNC).

In fact, the effectiveness of treatment depends on the possibility of correctly positioning the catheter.

In particular, in the case of atomization, the device should be able of positioning the tip of the atomizing catheter in a proper relative position and with a proper orientation with respect to the vocal chords.

No suitable systems are available at the state of the art. In fact current medical devices such as oro-pharyngeal cannulae, e.g Mayo cannula, and laryngeal mask only address the problem of maintaining the airways opened.

In particular, the Mayo cannula does not allow a proper positioning of the catheter and does not help in keeping such catheter in the right position relatively to the pharyngeal walls; furthermore the morphology of the cannula creates an obstacle to the passage of air, when used during ventilation modalities through the nose (e.g. nasal CPAP) or when applied to spontaneously breathing patients.

GB 2444779 discloses a laryngeal mask lung ventilation in a patient, comprising a conduit adapted to direct a liquid substance through the glottic opening, into the trachea.

Document WO 2012/032290 A1 discloses a laryngeal mask adapted for liquid drug delivery using a catheter: with such a device it is possible to correctly positioning the catheter thanks to its shape. However, since it seals around the circumference of the laryngeal inlet, said device has the drawback of completely preventing the passage of air through the nose, thus being incompatible with non-invasive modalities of ventilation commonly used on infants (e.g. nasal CPAP or HFNC) or with the use of the catheter in spontaneously breathing patients.

In co-pending, unpublished patent application PCT/EP2016/059422 a possible solution is disclosed. However, even if effective in several cases, the inventors have found out that such solution may be associated to some degree of discomfort, especially when the baby is active and fully awake. Moreover, with the prior art the baby needs to keep a fixed relative position between the head and the shoulders for the full duration of the treatment.

OBJECTS OF THE INVENTION

It is an object of the present invention a new device able to overcome at least some of the problems associated with the prior art.

SUMMARY OF THE INVENTION

The present invention provides a devices and methods as set out in the accompanying claims. According to one aspect of the present invention, we provide a device for facilitating the positioning of a catheter for the delivery of liquid medicament to spontaneously breathing patient, including:
an elongated main body adapted to follow the internal shape of the patient's upper airways, the elongated main body being made of a flexible and resilient material and having a proximal end which is thinner than the distal end, the elongated main body growing progressively its size towards the rounded shaped distal end, the distal end being adapted to engage the internal wall of the patient's deep part of the pharynx;
guiding means provided within the elongated main body and adapted to house a catheter;
at least one opening obtained within the elongated main body, the at least one opening creating a passage in the cranium-caudal direction in order to create a low resistance path for the breathing air between the nose and the lungs. In particular, the tip of the atomizing catheter should preferably be placed few millimeters above the vocal chords and it should be pointing towards the inlet of the trachea, to avoid the injection of the atomized drug into the esophagus or on the pharynx walls, wasting it. In addition, the device should keep the soft tissues of the pharyngeal wall away from the tip of the atomizing catheter, to allow it to atomize the medicament efficiently and not to trigger vagal reflexes.

In a preferred embodiment of the present invention the device further comprises positioning means for fixing the device to the patient. Such positioning means can include a substantially plate shaped element, which can be useful to hold the device in place. Preferably, the positioning means should be made of elastic material and be able to allow to get fixed to the elongated body at different distances.

The material of the elongated body should be preferably a flexible and resilient material, selected e.g. among the following: medical grade silicone, natural medical rubber, which could be latex or latex-free, synthetic medical rubber.

In a preferred embodiment the guiding means include a passing through hole having a preferable diameter between 0.5 mm and 4 mm, or preferably between 0.5 and 2.5 mm, in order to allow the housing of the atomizing catheter.

Moreover, in another preferred embodiment the elongated body is provided with open channels that can be used to sample pressure or provide gas or fluids or both to or from the pharyngeal space to or from the outside part of the device.

In the present disclosure the term "patient" can be applied to any mammal such as a human patient and a non-human primate as well as experimental animals such as piglets and lambs, preferably to a spontaneously breathing human patient, more preferably to a spontaneously breathing preterm neonate.

Preferably, the medicament comprises an exogenous pulmonary surfactant, e.g. selected from the group consisting of modified natural pulmonary surfactants (e.g. poractant alfa), artificial surfactants, and reconstituted surfactants.

According to a second aspect, the present invention concerns the use of the aforementioned device in combination with a catheter for the delivery of a medicament to spontaneously breathing patients.

In a third aspect of the invention, we provide a method for preventing and/or treating a respiratory distress syndrome in a spontaneously breathing patient, said method comprising the step of applying the aforementioned device in combination with a catheter for the delivery of a medicament.

In a particular embodiment, said catheter is mounted on a system for delivering by atomization a medicament in the retro- or pharyngeal region of the patient. More preferably, the method of the invention comprises applying to the patient a non-invasive ventilation modalities such as nasal Continuous Positive Airway Pressure (nCPAP) or HFNC.

In a fourth aspect of the invention, we provide a kit comprising: a) a catheter; b) the above described device for positioning and/or facilitating the introduction of the catheter into the mouth and pharynx of a patient; c) a medicament and d) container means for containing the medicament, the device and the catheter.

The method and system according to preferred embodiments of the present invention allows and facilitates the correct positioning of a catheter for the delivery of a liquid medicament (e.g. surfactant). The method and system of the present invention provides several advantages including: 1) non-invasive operation in spontaneously breathing patients also in combination with mechanical ventilation; 2) minimized patient discomfort and 3) it allows movements of the neck of the patient during the treatment.

BRIEF DESCRIPTION OF THE DRAWINGS

Reference will now be made, by way of example, to the accompanying drawings, in which:

FIG. 1A shows an isometric view of a device before deployment in the patient, according to an embodiment of the present invention;

DEFINITIONS

With the term "pulmonary surfactant" it is meant an exogenous pulmonary surfactant administered to the lungs that could belong to one of the following classes:
i) "modified natural" pulmonary surfactants which are lipid extracts of minced mammalian lung or lung lavage. These preparations have variable amounts of SP-B and SP-C proteins and, depending on the method of extraction, may contain non-pulmonary surfactant lipids, proteins or other components. Some of the modified natural pulmonary surfactants present on the market, like Survanta are spiked with synthetic components such as tripalmitin, dipalmitoylphosphatidylcholine and palmitic acid.
ii) "artificial" pulmonary surfactants which are simply mixtures of synthetic compounds, primarily phospholipids and other lipids that are formulated to mimic the lipid composition and behavior of natural pulmonary surfactant. They are devoid of pulmonary surfactant proteins;
iii) "reconstituted" pulmonary surfactants which are artificial pulmonary surfactants to which have been added pulmonary surfactant proteins/peptides isolated from animals or proteins/peptides manufactured through recombinant technology such as those described in WO 95/32992 or synthetic pulmonary surfactant protein analogues such as those described in WO 89/06657, WO 92/22315, and WO 00/47623.
The term "non-invasive ventilation" (NIV) procedure defines a ventilation modality that supports breathing without the need for intubation.

The term "prophylaxis" refers to the use for reducing the occurrence of the disease, while the term "treatment" refers to the use for palliative, curing, symptom-allievating, symptom-reducing, disease regression-inducing therapy.

The term "pre-term neonate" refers to a baby whose birth occurs earlier than 37 weeks gestational age.

The term "facilitating" means the capacity of a device to allow an easy and safe introduction of a catheter into the mouth/throat of the patient.

The terms "flexible and resilient" mean capable of being bent or flexed and capable of regaining its original shape or position after bending, stretching, compression, or other deformation.

The term "teardrop shaped" means a shape characterized by having a globular form at the bottom and tapering to a point at the top: something that is shaped like a falling tear.

DETAILED DESCRIPTION OF PREFERRED EMBODIMENTS

Figure 1A:
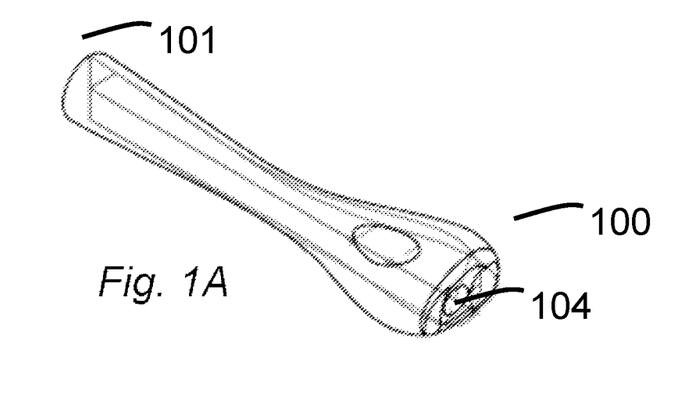
Figure 1B:
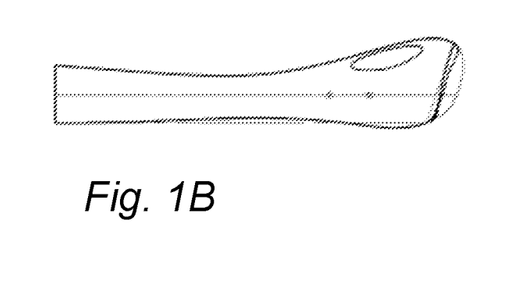
FIG. 1B shows a front view of a device before deployment in the patient, according to an embodiment of the present invention.
Figure 1C:
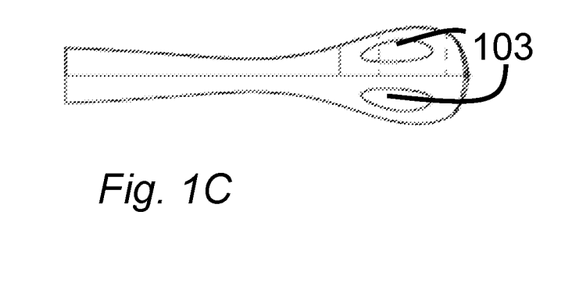
FIG. 1C shows a superior view of a device before deployment in the patient, according to an embodiment of the present invention.
Figure 2A:
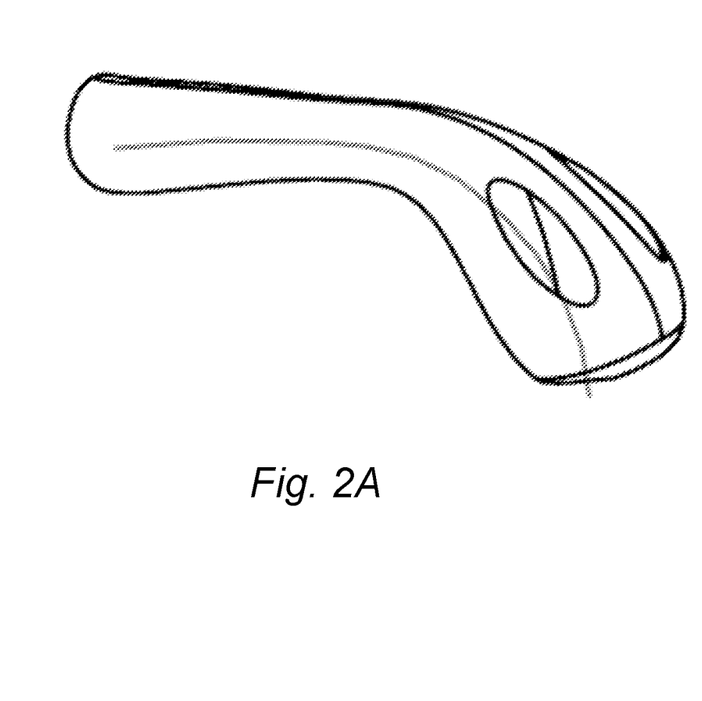
FIG. 2A shows an isometric view of a bended device as deployed to the patient, according to an embodiment of the present invention.
Figure 2B:
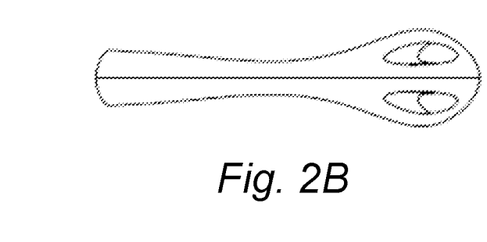
FIG. 2B shows a frontal view of a bended device as deployed to the patient, according to an embodiment of the present invention.
Figure 2C:
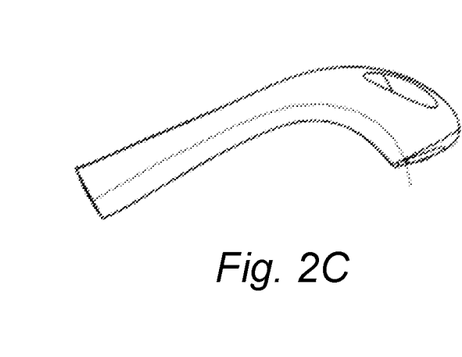
FIG. 2C shows a lateral view of a bended device as deployed to the patient, according to an embodiment of the present invention.
Figure 2D:
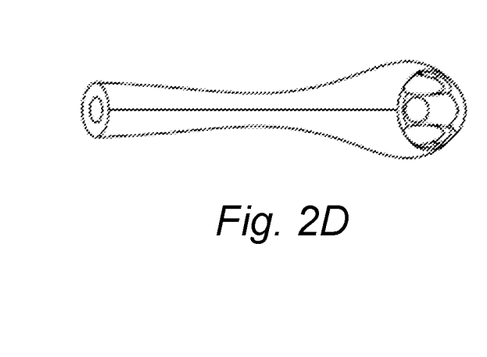
FIG. 2D shows a bottom view of a bended device as deployed to the patient, according to an embodiment of the present invention.
Figure 3:
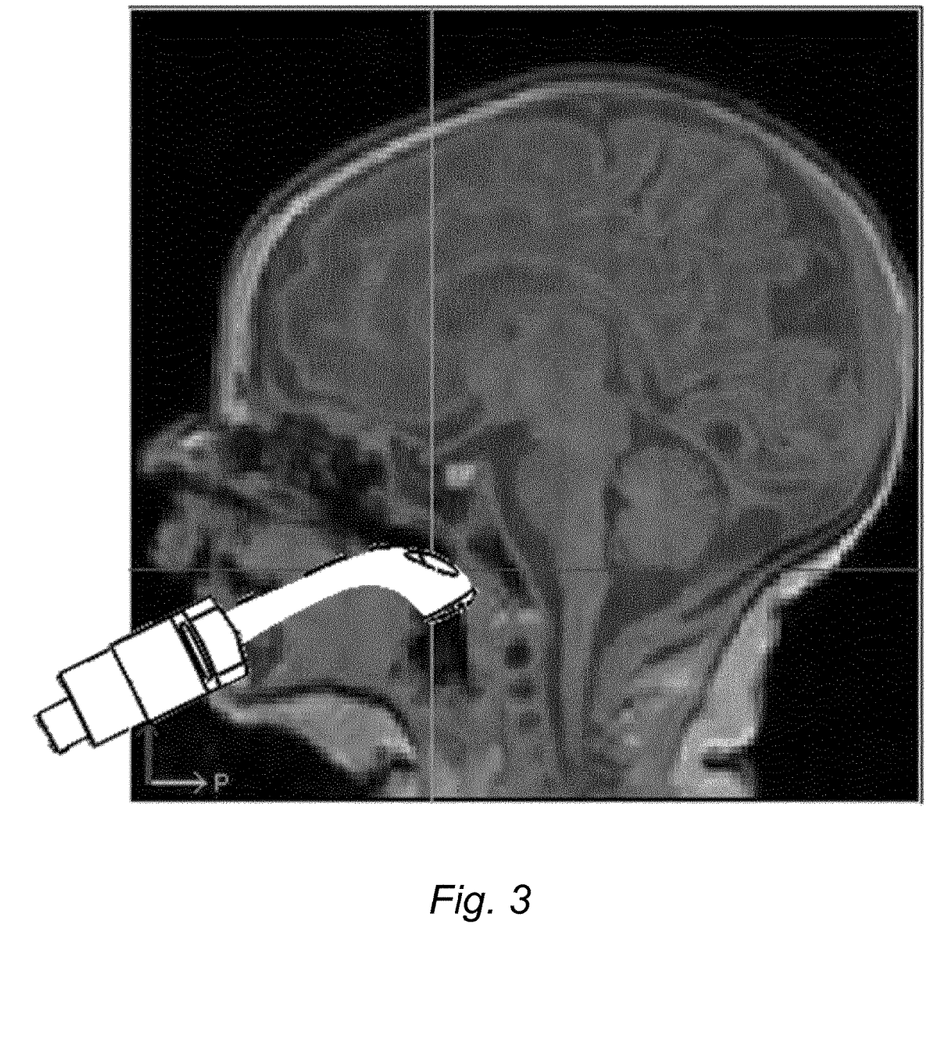
FIG. 3 shows a sagittal view of the bended device over imposed to an MM image of a patient once the interface is deployed.

According to an embodiment of the present invention, a flexible device as the one represented in FIGS. 1A, 1B, and 1C provides a support for positioning and for keeping in the correct place a catheter which may be used to deliver drug to the lung. In a preferred embodiment of the present invention, device is provided with guiding means (e.g. a passing through hole) which can house a catheter for the administration of liquid or aerosol medicament.

As shown in FIG. 1 the device 100 according to the present invention comprises the following components: an elongated body, "teardrop" shaped, for guiding and holding the catheter in the desired position and orientation, the main body (e.g. stem) is thin in the proximal part 101 and it enlarges in the distal part, the distal part being designed in order to accommodate itself in a reproducible position in the patient's pharyngeal cavity; a pathway 103 for allowing the passage of air from the nose to the trachea and vice-versa, that is carved into the main body and guiding means 104 (e.g. a passing-through hole).

The rationale supporting the design is: 1) the need to avoid mechanical stimulation in the pharynx that can trigger vagal stimulation, 2) need for self-positioning and resilience to the head movements of the patient in order to improve the comfort, 3) allowing spontaneous breathing from the nose 4) creating a direct pathway for a drug or a catheter from the mouth of the patient to his/her pharyngeal region.

In order to reduce the mechanical stimulus triggered by an external body in the region of the pharynx, the contact pressure between the pharyngeal walls and a foreign body should be distributed on a surface as large as possible, as it happens when the bolus of food is swallowed. In that case, the passage of the bolus in the pharynx region is even perceived as pleasant. Therefore, the final part of the device should be designed to avoid sharp variation in the curvature radius. Besides, the enlarged part helps even self-positioning of the interface, because once the enlarged part reaches the pharynx, its increased dimensions prevent the part from further movements towards the trachea. In a preferred embodiment, the enlarged part is asymmetrical in the sagittal plane, showing an enlargement more pronounced in the posterior region to better fit the anatomy of the pharynx; consequently, the increased enlargement improves the engagement of the pharynx and promotes stability, preventing the rotation of the interface once it is in loco. Beside, this design allows resilience to movement of the head too, in fact, once the pharynx is engaged, small movement of the head doesn't affect anatomically the pharynx region, and then even if the thin part follows the movement of the head, the enlarged part is stable in the pharynx.

In case of new born patients self-positioning is also warranted when the patient is awake by exploiting the suction reflex of the babies. In fact, although the babies are preterm, they have already developed a strong suction reflex that applies to whatever is placed in their mouth in response to the evolutionary need of promoting maternal breastfeeding. This attitude is already known and exploited for clinical procedure such as finger intubation in which the operator inserts his/her finger into the mouth of the infant and then the baby's suction reflex drags the finger in place up to the inlet of the trachea. The same reflex can be exploited with the interface.

To this aim, the shape of the device is designed accordingly to the anatomy of the upper-airways of the baby and made of a soft deformable, but resilient material such as medical grade silicone but it is preferably not pre-bended: this happens because the interface should be put in the mouth of the baby, enlarged part first, and then it will be actively dragged in position by the patient's suction reflex without requiring the operator to further manoeuvres the interface but just the application of a light guidance and support from outside the mouth of the patient. FIGS. 2A, 2B, 2C, 2D and 3 show the interface as it bends once deployed into the patient. Briefly, once the interface is placed in the mouth of the patient, the suction reflex drags it to its position where it gets stuck thanks to the final enlargement and the fit of the enlarged part of the elongated body of the interface in the pharyngeal cavity. In the present example the material used is medical grade silicone, however those skilled in the art will appreciate that other materials, ideally flexible and resilient, could be used instead, for example a material selected among the following: medical grade silicone, natural medical rubber, which could be latex or latex-free, synthetic medical rubber.

Because of the "open" structure realized by to the one or more opening in the final (larger) part of the device, it does not prevent the passage of the air and, therefore, the delivery of the medicament by means of the catheter can be simultaneous to spontaneous breathing, respiratory support (such as CPAP of HFNC) or non-invasive mechanical ventilation (NIV).

Accordingly to this aim, the cut or plurality of cuts crossing the enlarged part of the elongated body should be as wide as possible, considering a trade-off between to provide sufficient mechanical stability to the device and to minimize the resistance to the breathing flow coming from the nose.

The main body extends from the mouth of the patient to the retro-pharynx, with a shape that fits the anatomy of the upper airways of the patient. The main body is intended: 1) to guide and hold an atomizing catheter conveying the medicament from the mouth to the retro-pharynx in the proper position and with a specific orientation; 2) to allow the handling and insertion of the system and to contribute to keep the proper position of the device 100 thanks to its shape that follows the anatomy of the upper airways of the patient.

Accordingly, the skilled person in the art shall modify the shape of the stem in order to follow the anatomy of the upper airway of patient.

In order for the device 100 to provide proper guidance to a catheter it is necessary a housing where the catheter can be inserted or positioned and properly pointed towards the inlet of the trachea. Such housing can be a lumen (i.e. a passing through hole 104 as mentioned above) which can develop along the stem or, in an alternative embodiment, it can develop along a different line to 1) reduce the curvature for the catheter and to ease the insertion of the catheter and/or 2) provide the appropriate direction of the catheter tip, in order to deliver the medicament in the patient's inlet of the trachea.

The person skilled in the art shall select the inner diameter of the passing-through hole 104 depending on the diameter of the utilized catheter. Being the main body relatively large and not pre-bended, the room offered to host a catheter is big enough to allow the passage of a catheter up to 4 mm of diameter In a preferred embodiment, the shape of the device, in particular the shape of the enlarged element, helps in the positioning of the device itself within the patient's larynx: it should be avoided that the device can be pushed too far down the larynx, otherwise it would stimulate lot of reflexes that induce laryngo-spasms or glottis closure leading to alteration of normal breathing pattern (e.g. reduction of respiratory rate).

On the other hand, if the device is not deep enough in the pharynx the medicament (e.g. a surfactant) deposits on the pharynx walls and is subsequently swallowed by the patient, preventing to get it into the lung.

Also, it should be considered that the area where the device enters into contact with the patient is very sensitive.

In a preferred embodiment of the present invention, the device should have dimensions determined by the anatomy, in particular considering the example of a human pre-term neonate as a patient: 1) part of the stem extends from the mouth to the retro pharynx, so the length of this part can be from 40 to 60 mm, depending on the weight of the patient, 2) the part of the stem outside the mouth is from 30 to 70 mm long, it is used to keep in place the catheter and to make easier the handling, 3) the diameter of the elongated body is from 5 mm to 8 mm in the outer part and increases to a minimum of 8 mm and maximum of 15 mm in the larger part of the 'teardrop' shape device.

When the device of the present invention is used in combination with a catheter mounted on an atomizing device, the stem will also provide a correct placement for said atomizing catheter, whose distal tip should be few millimeters above the vocal chords, and a proper direction of the atomizing tip, as it should point towards the trachea and not towards the esophagus or laryngeal/pharyngeal walls.

The cross section of the stem can be an ellipse or any rounded smoothed shape (see FIGS. 1A, 1B, 1C, 2A, 2B, 2C, and 2D). The interface should be made of soft and malleable material, like medical grade silicone, in a rounded shaped, in order to provide tolerability and comfort. Besides, thanks to the softness of the material, small movements of the head of the baby should not change the position of the interface or inducing discomfort.

One of the advantages of the device according to the present invention is that the passage of the air is not prevented by the shape of the device, therefore any cut into the enlarged part that allow the passage of the air from the nose are acceptable alternative. The cut or cuts in the enlarged part may assume different shapes as shown in FIG. 4, which are designed to better fit slightly differences in the anatomy.

Figure 4:
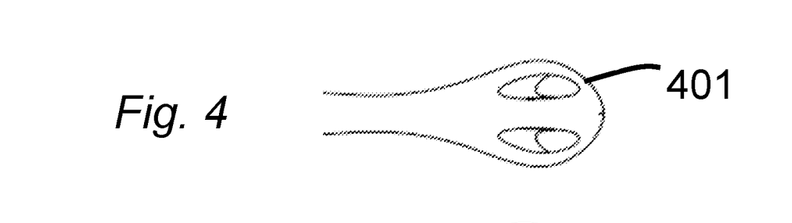
FIG. 4 shows an example of the openings according to a possible embodiment of the present invention.
Figure 6:
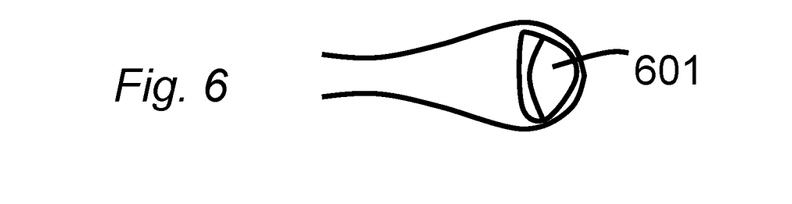
FIG. 6 shows an example of the openings according to a possible embodiment of the present invention.
Figure 7:
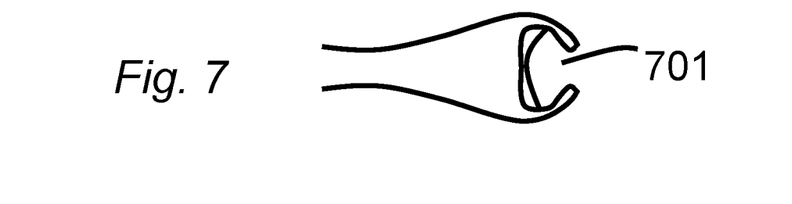
FIG. 7 shows an example of the openings according to a possible embodiment of the present invention.

In particular, FIG. 4 shows an example of a double passage 401, FIG. 6 shows an example of a single cut 601, and FIG. 7 shows an example of an extended cut that opens the enlarged part to maximize the passage of air 403. The orientation of the plane of the cross section of the enlarged part in its maximum compared to the stem should be driven by the anatomy to allow the catheter be properly pointed toward the trachea.

Accordingly, the skilled person in the art shall adapt the orientation of the plane of the ring compared to the stem depending on the anatomy of the patient.

Figures 5A, 5B:
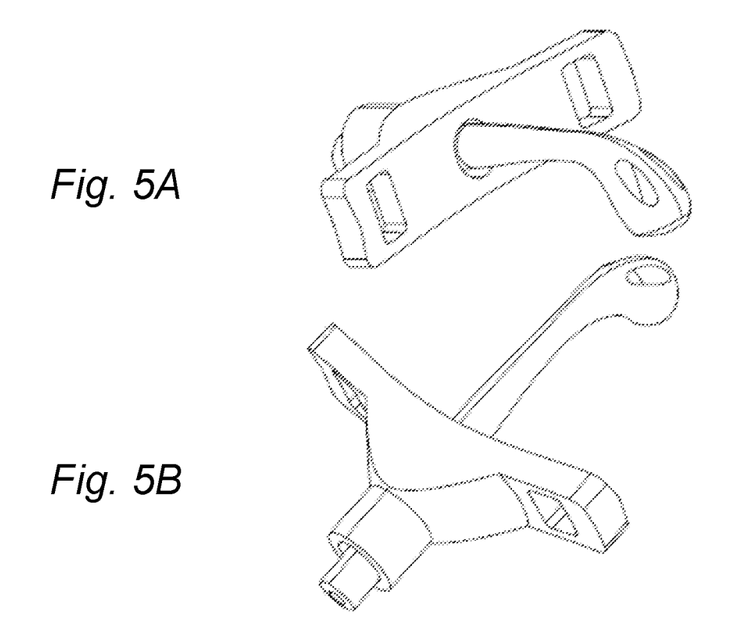
FIG. 5A shows an example of the optional positioning element according to an embodiment of the present invention.
FIG. 5B shows an example of the optional positioning element according to an embodiment of the present invention.

Optionally, another component of the device is made of a plate connected to the smaller part of the elongated body through a connector allowing changes in the length of the part of the stem between the plate and the tip of the device as shown in FIGS. 5A and 5B. The plate is kept outside of the mouth and helps in maintaining the whole device in the proper position limiting the leaks from the mouth and, therefore, facilitating the maintenance of a close-mouth condition during administration of the treatment. This latter condition is desirable because 1) it is more physiological, 2) it allows the delivery of a constant known pressure during CPAP therapy and 3) it maximizes the pressure swings at the pharynx, improving, therefore, the efficiency of the systems that can be used to identify the phase of the breath in order to synchronize the delivery of the treatment during inspiration only.

In a preferred embodiment, the positioning device can move along the stem in order to be placed in the right position depending on the size of the baby and it is made of soft material such as medical grade silicone.

In the present application we addressed the problem of delivering the right amount of atomized medicament to a patient, e.g. a preterm neonate, by minimising the possible discomfort to the patient. In a preferred embodiment, the medicament is a pulmonary surfactant, e.g. an exogenous pulmonary surfactant.

In this respect, any pulmonary surfactant currently in use, or hereafter developed for the prophylaxis and/or treatment of Respiratory Distress Syndrome (RDS) or other pulmonary conditions related to the deficiency of endogenous pulmonary surfactant could be suitable for use in the present invention. These include modified natural, artificial and reconstituted pulmonary surfactants (PS).

Current modified natural pulmonary surfactants include, but are not limited to, bovine lipid pulmonary surfactant (BLES™, BLES Biochemicals, Inc. London, Ont), calfactant (Infasurf™, Forest Pharmaceuticals, St. Louis, Mo.), bovactant (Alveofact™, Thomae, Germany), bovine pulmonary surfactant (Pulmonary surfactant TA™, Tokyo Tanabe, Japan), poractant alfa (Curosurf®, Chiesi Farmaceutici SpA, Parma, Italy), and beractant (Survanta™, Abbott Laboratories, Inc., Abbott Park, Ill.)

Examples of artificial surfactants include, but are not limited to, pumactant (Alec™, Britannia Pharmaceuticals, UK), and colfosceril palmitate (Exosurf™, GlaxoSmithKline, plc, Middlesex).

Examples of reconstituted surfactants include, but are not limited to, lucinactant (Surfaxin™, Windtree Inc., Warrington, Pa.) and the product having the composition disclosed in Table 2 of Example 2 of WO 2010/139442, whose teaching is incorporated herein by reference.

Advantageously, the pulmonary surfactant is a modified natural surfactant or a reconstituted surfactant. More preferably the pulmonary surfactant is poractant alfa (Curosurf®). In another preferred embodiment, the reconstituted surfactant has composition disclosed in WO 2010/139442 (see Table 2 of Example 2).

Preferably, the pulmonary surfactant is administered as a suspension in a sterile pharmaceutically acceptable aqueous medium, preferably in a buffered physiological saline (0.9% w/v sodium chloride) aqueous solution.

Its concentration shall be properly adjusted by the skilled person in the art.

Advantageously, the concentration of the surfactant might be comprised between 2 and 160 mg/ml, preferably between 10 and 100 mg/ml, more preferably between 40 and 80 mg/ml.

The dose of the pulmonary surfactant to be administered varies with the size and age of the patient, as well as with the severity of the patient's condition. Those of skill in the relevant art will be readily able to determine these factors and to adjust the dosage accordingly.

Other active ingredients that could advantageously be comprised in the medicament according to the invention include those currently used for the prevention and/or treatment of neonatal respiratory diseases, for example inhaled corticosteroids.

The present invention also concerns the use of the device herein disclosed in combination with a catheter for the delivery of a medicament to spontaneously breathing patients.

In a particular embodiment, a catheter for minimally invasive endotracheal administration of a pulmonary surfactant could be utilized, for example according to procedure disclosed in WO 2008/148469 or in Dargaville P A et al Arch Dis Fetal Neonatal Ed 2013, 98(2), 122-126. Said catheter should have a diameter equal to or lower than 5 French (hereinafter Fr) corresponding to about 1.66 mm (1 French corresponds to ⅓ mm). Advantageously the diameter shall be comprised between 2.0 and 5.0 Fr. Preferred diameters would be 3.5, 4.0 and 5.0 Fr.

To act as a catheter according to the invention, any gastric or nasogastric tube, arterial or suction catheter of common use in hospitals can be utilized. It may be made of any material, preferably of polyurethane or silicone, and could have a length comprised from 10 to 35 cm, preferably of 15 cm or 30 cm.

In another particular embodiment, the catheter is mounted on a system for delivering by atomization a medicament in the retro- or pharyngeal region such as that disclosed in WO 2013/160129. Preferably, the delivery of the atomized medicament is done by means of an air blasting technique. Using air to assist atomization is a well-known technique that grants a fully developed atomization also when low pressure and low flow conditions are required (see e.g. Arthur Lefebvre, "Atomization and spray", Taylor and Francis, 1989). Such technique is based on a relatively small amount of gas (e.g. air, but it could be other compressed gas, e.g. oxygen, nitrogen, or helium) which flows in one or more separate channels than the medicament which is delivered in a liquid form; the air flow accelerates and breaks the liquid column, inducing the atomization of the medicament. Therefore the multi-lumen catheter includes a plurality of channels (at least two, one for the medicament and one for the air) for conveying contemporarily the medicament and the air flow. The liquid medicament column is broken up in droplets by the turbulence due to the air flowing next or around when the two flows (air and liquid medicament) exit the catheter channels and meet in the retro-pharyngeal region. The atomized droplets have a median diameter of at least 20 micron, preferably equal to or higher than 40 micron, more preferably equal to or higher than 60 micron. It is believed that this effect is caused by the air flow which accelerates the fluid sheet instability. The air also helps in dispersing the droplets, preventing collision among them and facilitating the diffusion of the medicament in the lungs by reducing the likelihood of contact between the particles and the wall of the retropharyngeal cavity.

In a preferred embodiment, the multi-lumen catheter could present a length of 7-15 cm and an internal diameter of 0.6-0.8 mm. According to a more preferred embodiment the lumen through which the medicament passes has a diameter of 0.75 mm, while the lateral lumen for gas may be a single lumen for all the length of the catheter except for the 5 distal millimetres at the tip, where it can change its shape into a plurality of lumens coaxial to the surfactant lumen.

Alternatively, the multi-lumen catheter disclosed in the co-pending application EP 13189768.8 whose teaching is incorporated herein by reference, could be utilized.

In a preferred embodiment of the invention, the device herein disclosed is used in combination with a multi-lumen catheter conveying the atomized medicament (e.g. a pulmonary surfactant) directly to the retro-pharyngeal region in order to increase efficiency of the medicament administration without being invasive: this is particularly important for very young patients, such as pre-term neonates suffering from neonatal Respiratory Distress Syndrome (nRDS). Advantageously, the device of the invention is used for administering a medicament through a catheter to any spontaneously breathing patient, more advantageously to a spontaneously breathing human neonate, preferably to pre-term neonate. In a particular embodiment, the device of the invention is used for administering a medicament through a catheter to pre-term very-low-birth-weight-neonates of 24-35 weeks gestational age that are spontaneously breathing, and demonstrate early signs of respiratory distress syndrome as indicated either by clinical signs and/or supplemental oxygen demand (fraction of inspired oxygen ($FiO_2$) >30%).

In a further aspect of the invention, a method for preventing and/or treating a respiratory distress syndrome in a spontaneously breathing patient is provided, said method comprising applying the device herein disclosed in combination with a catheter a for the delivery of a medicament. However, the therapeutic method could also be intended for the prevention and/or treatment of any disease related to a surfactant-deficiency or dysfunction as well as of conditions in which respiratory distress may be present that include, but are not limited to, meconium aspiration and pulmonary infection. Preferably, the method of the invention comprises applying to the patient a non-invasive ventilation procedure such as nasal Continuous Positive Airway Pressure (nCPAP). Advantageously, nasal Continuous Positive Airway Pressure (nCPAP) is applied to said patients, according to procedures known to the person skilled in the art.

Preferably a nasal mask or nasal prongs are utilised. Any nasal mask commercially available may be used, for example those provided by The CPAP Store LLC, and the CPAP Company.

Nasal CPAP is typically applied at a pressure comprised between 1 and 12 cm water, preferably 2 and 8 cm water, although the pressure can vary depending on the neonate age and the pulmonary condition.

Other non-invasive ventilation procedures such as nasal intermittent positive-pressure ventilation (NIPPV) and bi-level positive airway pressure (BiPAP) or high flow nasal cannula (HFNC) can alternatively be applied to the patients.

It will be appreciated that alterations and modifications may be made to the above without departing from the scope of the disclosure. Naturally, in order to satisfy local and specific requirements, a person skilled in the art may apply to the solution described above many modifications and alterations. Particularly, although the present disclosure has been described with a deep degree of particularity with reference to preferred embodiment(s) thereof, it should be understood that eventual omissions, substitutions and changes in the form and details as well as other embodiments are possible; moreover, it is expressly intended that specific elements and/or method steps described in connection with any disclosed embodiment of the disclosure may be incorporated in any other embodiment as a general matter of design choice.

The invention claimed is:

1. A device for facilitating positioning of a catheter for delivery of a liquid or aerosol pulmonary surfactant to a lung of a spontaneously breathing patient, the device including:
   an elongated main body integrally formed of a same material, configured to extend from the mouth of the patient to the retro-pharynx of the patient, and configured to follow the internal shape of the upper airways of the patient, the elongated main body being made of a flexible and resilient material, the elongated main body having a proximal end and a rounded shaped distal end, the proximal end being thinner than the rounded shaped distal end, the elongated main body growing progressively in size towards the rounded shaped distal end such that the elongated main body is teardrop shaped, and the rounded shaped distal end being configured to engage the internal wall of a deep part of the pharynx of the patient;
   guiding means provided within the elongated main body, configured to house the catheter, configured to provide a correct placement of a catheter tip of said catheter a few millimeters above the vocal chords of the patient, and configured to provide a proper direction of the catheter tip towards the trachea of the patient; and
   at least one opening within the rounded shaped distal end, the at least one opening, in use, creating a passage in the cranium-caudal direction in order to create a low resistance path for breathing air between the nose and the lung of the patient,
   wherein a portion of the rounded shaped distal end extends beyond an opening of the guiding means in the rounded shaped distal end.

2. The device of claim 1, wherein the at least one opening includes two parallel openings towards the rounded shaped distal end of the elongated main body, which ensure airflow through the natural airways of the patient.

3. The device of claim 1, further comprising positioning means for fixing the device to the patient.

4. The device of claim 3, wherein the positioning means include a substantially plate shaped element.

5. The device of claim 1, wherein the material of the elongated main body includes a material selected among the following: grade silicone, natural latex medical grade rubber, natural latex-free medical grade rubber, and synthetic medical grade rubber.

6. The device of claim 1, wherein the guiding means includes a passing through hole.

7. The device of claim 6, wherein the passing through hole has a diameter of 0.5 mm to 4 mm.

8. The device of claim 1, further including at least one open channel within the elongated main body adapted to sample a pressure in the pharynx.

9. A system, comprising:
   the catheter configured to deliver the pulmonary surfactant; and
   the device of claim 1,
   wherein the catheter is positioned within the device.

10. The system according to claim 9, further comprising:
    the pulmonary surfactant, wherein the pulmonary surfactant is selected from a group consisting of a modified natural pulmonary surfactant, an artificial surfactant, and a reconstituted surfactant.

11. The system according to claim 9, wherein the patient is a spontaneously breathing pre-term neonate.

12. A method, comprising:
providing the device of claim 1 for positioning the catheter for the delivery of the pulmonary surfactant; and
using the device.

13. A kit comprising:
a) a pharmaceutical composition comprising a pulmonary surfactant suspended in a pharmaceutically acceptable aqueous medium;
b) a flexible catheter for delivering the pulmonary surfactant;
c) the device of claim 1 for facilitating introduction and the positioning of the catheter into the retro-pharyngeal region; and
d) container means for containing the pharmaceutical composition, the system, and the positioning means.

* * * * *